United States Patent [19]

Basil et al.

[11] 4,201,790

[45] May 6, 1980

[54] BENZOPHENONE DERIVATIVES

[75] Inventors: Berkeley Basil, Highwood, Nr. Chelmsford; Kenneth R. H. Wooldridge, Brentwood, both of England

[73] Assignee: May & Baker Limited, Essex, England

[21] Appl. No.: 860,303

[22] Filed: Dec. 14, 1977

Related U.S. Application Data

[63] Continuation of Ser. No. 695,445, Jun. 14, 1976, abandoned.

[30] Foreign Application Priority Data

Jun. 20, 1975 [GB] United Kingdom ............... 26407/75

[51] Int. Cl.$^2$ ........................ A01N 9/20; A01N 9/24; C07C 93/06
[52] U.S. Cl. ............................... 424/330; 260/348.15; 260/348.57; 260/501.18; 260/501.19; 260/570 R; 424/316; 568/333
[58] Field of Search ........... 260/570.7, 570 R, 501.18, 260/501.19; 424/316, 330

[56] References Cited

U.S. PATENT DOCUMENTS

| 3,051,709 | 8/1962 | Shapiro et al. | 260/570.7 X |
| 3,501,769 | 3/1970 | Crowther et al. | 260/570 X |
| 3,875,149 | 4/1975 | Wooldridge et al. | 260/570 X |

*Primary Examiner*—Robert V. Hines
*Attorney, Agent, or Firm*—Stevens, Davis, Miller & Mosher

[57] ABSTRACT

Benzophenone derivatives of the formula:

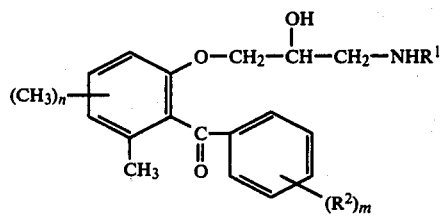

wherein $R^1$ is isopropyl, t-butyl or 2-phenylethyl, $R^2$ is methyl or chlorine, n is 1 or 2 and m is 0, 1 or 2, are new compounds possessing pharmacological properties especially indicative of utility in the treatment of migraine.

10 Claims, No Drawings

BENZOPHENONE DERIVATIVES

This is a continuation of application Ser. No. 695,445 filed June 14, 1976 and now abandoned.

This invention relates to new therapeutically useful benzophenone derivatives, to a process for their preparation, and to pharmaceutical compositions containing them.

It is known, for example from United Kingdom Pat. Specifications Nos. 994918, 995800, 1021522, 1023214, 1046001, 1047927, 1058822, 1066613, 1069341, 1069342, 1069345, 1079989, 1089769, 1123258, 1127469, 1128052, 1129072, 1206420, 1231783, 1247384, 1269776, 1327707 and 1362228, that many 1-amino-3-aryloxy-2-propanol derivatives possess β-adrenergic blocking properties and are therefore useful in the treatment or prophylaxis of heart diseases, such as angina pectoris and cardiac arrhythmias, and in the treatment of hypertension and phaeochromocytoma, in man. It is also known that small differences in structure between said derivatives are often accompanied by relatively large differences in their pharmacological properties.

It is the object of the present invention to provide a new small class of 1-amino-3-aryloxy-2-propanol derivatives carrying in the ortho-position of the aryloxy (specifically phenoxy) ring a benzoyl group, viz. benzophenone compounds, which have particularly valuable pharmacological properties.

According to the present invention, there are provided the new benzophenone derivatives of the general formula:

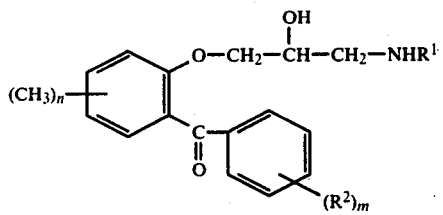

(wherein $R^1$ represents an isopropyl, t-butyl or 2-phenylethyl group, $R^2$ represents a methyl group or a chlorine atom, n represents 1 or 2 and m represents 0, 1 or 2) and non-toxic acid addition salts thereof. It is to be understood that when m represents 2 then the substituents represented by the symbol $R^2$ may be the same or different.

The compounds of formula I exist in stereoisomeric forms, and the present invention includes all such forms and mixtures thereof, including racemic forms, and their non-toxic acid addition salts.

Compounds of general formula I which are of especial importance are the following:

DL-1-(2-benzoyl-3,5-dimethylphenoxy)-2-hydroxy-3-isopropylaminopropane, (A);

DL-1-(3,5dimethyl-2-p-toluoylphenoxy)-2-hydroxy-3-isopropylaminopropane, (B)

DL-1-(2-benzoyl-3,5,6-trimethylphenoxy)-2-hydroxy-3-isopropylaminopropane, (C);

DL-1-(3,5-dimethyl-2-o-toluoylphenoxy)-2-hydroxy-3-isopropylaminopropane, (D);

DL-1-[2-(2,6-dimethylbenzoyl)-3,5-dimethylphenoxy]-2-hydroxy-3-isopropylaminopropane, (E);

DL-1-[2-(2,4-dimethylbenzoyl)-3,5-dimethylphenoxy]-2-hydroxy-3-isopropylaminopropane, (F);

DL-1-(2-benzoyl-3,6-dimethylphenoxy)-2-hydroxy-3-isopropylaminopropane, (G);

DL-1-(2-p-chlorobenzoyl-3,5-dimethylphenoxy)-2-hydroxy-3-isopropylaminopropane, (H);

DL-1-t-butylamino-3-(3,5-dimethyl-2-p-toluoylphenoxy)-2-hydroxypropane, (I);

DL-1-(3,5-dimethyl-2-p-toluoylphenoxy)-2-hydroxy-3-(2-phenylethylamino)propane, (J), and non-toxic acid addition salts thereof, for example the hydrochloride salts. Compounds A and B and their non-toxic acid addition salts are of particular importance.

The letters of the alphabet A to J are assigned to the compounds for easy reference later in the specification, for example in the following Tables.

The new benzophenone derivatives of general formula I and their non-toxic acid addition salts possess valuable pharmacodynamic properties. For example, they exhibit a valuable vascular β-adrenoceptor blocking effect combined with a relatively low cardiac β-adrenoceptor blocking effect of lesser duration. This combination of properties is indicative of utility in the treatment of conditions wherein a vascular β-adrenoceptor blocking effect is desired but wherein a cardiac β-adrenoceptor blocking effect is not beneficial or may be harmful and may, therefore, be disadvantageous. In particular, the said combination of properties is indicative of utility in the treatment of migraine, which is believed to be caused by focal vasoconstriction in the cortex of the brain, followed by vasodilation which is associated with the symptoms of migraine, and in which block of cardiac β-adrenoreceptors is not beneficial, may be harmful and may, therefore, be disadvantageous.

These properties have been demonstrated in the following laboratory screening methods:

β-Adrenoceptor-blocking activity

Test I. β-Adrenoceptor blocking activity in the anaesthetised cat (intravenous administration).

Cats were anaesthetised with a mixture of pentobarbitone (6–12 mg./kg.) and chloralose suspension (80 mg./kg.) administered intraperitoneally. The heart rate was recorded from the E.C.G. or from the pulse, and blood pressure was recorded from the carotid artery. Whole (0.3–0.6 μg.) and half (0.15–0.3 μg.) doses of isoprenaline were then administered, intravenously via the jugular vein, alternately at 7 minute intervals over a period of several hours. 210 seconds after a half dose of isoprenaline, one of the compounds under test was administered intravenously. 210 seconds later the whole dose of isoprenaline was administered. The doses of the test compound required to reduce (1) the tachycardia and (2) the fall in diastolic blood pressure produced by the whole dose of isoprenaline to that produced by the half dose were determined. The former response gives a measure of the ability of the test compound to block β-adrenoceptors in the heart while the latter response gives a measure of the ability of the test compound to block the β-adrenoceptors mediating vasodilation.

The results obtained are shown below in Table I.

TABLE I

| Test Compound | i.v. Dose (mg./kg. animal body weight) | | Ratio cardiac dose vascular dose |
|---|---|---|---|
| | Cardiac | Vascular | |
| A* | 1.1 | 0.023 | 48 |
| B | 2.9 | 0.031 | 93.5 |

TABLE I-continued

| Test Compound | i.v. Dose (mg./kg. animal body weight) | | Ratio cardiac dose vascular dose |
|---|---|---|---|
| | Cardiac | Vascular | |
| C | 4.4 | 2.3 | 1.9 |
| D | 0.8 | 0.16 | 5.0 |
| E | 3.7 | 1.8 | 2.1 |
| F | 0.59 | 0.24 | 2.5 |
| G* | 7.1 | 4.2 | 1.7 |
| H* | 0.72 | 0.037 | 19 |
| I | 0.46 | 0.027 | 17 |
| J* | approx. 2.0 | 0.068 | 29 |

*Hydrochloride salt

Those hydrochloride salts of compounds A, G, H and J were dissolved in water and administered in aqueous solution. Compounds B, C, D, E, F and I were each dissolved in dilute aqueous hydrochloric acid solution (0.1 N) and the solution thus obtained was neutralised by treatment with aqueous sodium hydroxide solution (0.1 N), to give a neutral solution of the hydrochloride salt of the test compound suitable for administration.

Test II. β-Adrenoceptor blocking activity in the anaesthetised rhesus monkey and in the anaesthetised dog (intravenous administration)

Test compound A (hydrochloride salt) was tested intravenously in anaesthetised rhesus monkeys and dogs by proceeding in a similar fashion to that described above in Test I.

The results are expressed below in Table II.

TABLE II

| Animal | Dose (mg./kg. animal body weight) | | | |
|---|---|---|---|---|
| | 210 second interval after dose of test compound | | one hour interval after dose of test compound | |
| | cardiac | vasular | cardiac | vascular |
| Rhesus monkey | 0.1 | 0.0087 | >1 | 0.0076 |
| Dog | 0.1 | <0.02 | 0.13 | <0.02 |

Test III. β-Adrenoceptor blocking activity in the anaesthetised dog (oral administration)

Test compound A(hydrochloride salt) was tested orally in anaesthetised dogs by proceeding in a similar fashion to that described above in Test I and Test II. The results are expressed below in Table III.

TABLE III

| Time interval after dose of test compound | Oral dose (mg./kg. animal body weight) | |
|---|---|---|
| | cardiac | vascular |
| 1 hour | 4 | <0.1 |
| 2 hours | 3.2 | 0.08 |
| 3 hours | 6 | 0.1 |

Toxicity

In the above Tests I, II and III, the new compounds did not give rise to any acute side effects.

(i) Mouse; oral

Acute toxicity studies in the mouse show that DL-1-(3,5-dimethyl-2-p-toluoylphenoxy)-2-hydroxy-3-isopropylaminopropane (test compound B) has an $LD_{50}$ value of about 1000 mg./kg. animal body weight by oral administration.

(ii) Mouse; intravenous

The acute intravenous $LD_{50}$ figures observed in mice are shown in Table IV below.

TABLE IV

| Test Compound | A | B | C | D | E | F | H | I |
|---|---|---|---|---|---|---|---|---|
| i.v. $LD_{80}$ (mg./kg.) | 40 | 25-31 | 23 | 34 | 42 | 24 | 32-40 | 24 |

(iii) Rat; oral

Test compound A was well tolerated by four groups of rats, each of five males and five females, which received oral daily doses of 12, 24, 48 or 96 mg./kg. animal body weight during two weeks.

(iv) Dog; oral

Test compound A was well tolerated by three groups of beagles which received oral daily doses during two weeks. Two groups, each of two males and two females, each received a daily dose of 10 or 50 mg./kg. animal body weight and one group, of one male and one female, received a daily dose of 100 mg./kg. animal body weight.

According to a feature of the present invention, the benzophenone derivatives of formula I are prepared by the reaction of an epoxy compound of the general formula:

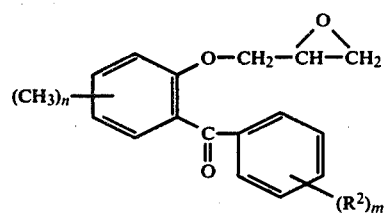

(wherein $R^2$, m and n are as hereinbefore defined) with an amine of the general formula:

$$R^1NH_2 \qquad \text{III}$$

wherein $R^1$ is as hereinbefore defined. The reaction may be carried out in an organic solvent, for example dimethylformamide or an alkanol containing from 1 to 4 carbon atoms, e.g. methanol, at a temperature between 0° C. and 100° C.

The epoxides of formula II employed as starting materials may be prepared by methods known per se for the preparation of epoxides, e.g. by the reaction of epichlorohydrin with a phenol of the general formula:

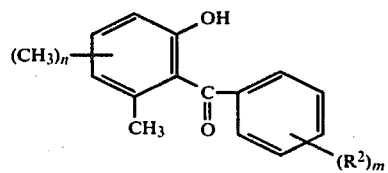

wherein $R^2$, m and n are as hereinbefore defined. The reaction may be carried out in an aqueous or inert organic solvent, for example dimethylformamide or an alkanol containing from 1 to 4 carbon atoms, e.g. methanol, in the presence of basic condensing agent, for example, potassium carbonate, sodium hydroxide or sodium methoxide, at a temperature between 0° C. and 100° C.

The phenols of formula IV may be prepared by methods known per se, or by analogous procedures, for the preparation of o-hydroxybenzophenones.

The benzophenone derivatives of general formula I may be converted by methods known per se into acid addition salts. Thus, the acid addition salts may be obtained by the action of an acid on the benzophenone derivatives in an appropriate solvent such as diethyl ether. The acid addition salt which is formed is precipitated, if necessary after concentration of its solution, and is separated by filtration or decantation.

For use in medicine, the benzophenone derivatives of general formula I are employed as such or in the form of non-toxic addition salts, i.e. salts containing anions which are relatively innocuous to the animal organism when used in pharmacodynamically effective doses so that the beneficial properties inherent in the bases are not vitiated by side-effects ascribable to the anions. Suitable non-toxic salts include salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and D-di-p-toluoyl tartrates.

By the term "methods known per se," as used in the present specification, is meant methods heretofore used or described in the chemical literature.

The following Examples illustrate the preparation of the new compounds of the invention.

EXAMPLE 1

Compound A

A mixture of 2-(2,3-epoxypropoxy)-4,6-dimethyl-benzophenone (35 g.), isopropylamine (40 ml.) and anhydrous methanol (200 ml.) was heated at reflux overnight. The solution was then evaporated in vacuo, and the residue was treated with an excess of anhydrous ethereal hydrogen chloride solution. The gum obtained was separated by decantation and triturated with anhydrous diethyl ether to give a solid (47.6 g.), m.p. 119°–121° C. The solid was dissolved in water. The solution obtained was allowed to stand at room temperature for 1 hour and was then shaken with ethyl acetate. The aqueous layer was separated, made alkaline by the addition of concentrated sodium hydroxide solution and extracted with ethyl acetate. The extract was dried over anhydrous sodium sulphate, and evaporated in vacuo. The oily residue was extracted with light petroleum (b.p. 60°–80° C.), and the extract was treated with anhydrous ethereal hydrogen chloride solution to give DL-1-(2-benzoyl-3,5-dimethylphenoxy)-2-hydroxy-3-isopropylaminopropane hydrochloride (29.4 g.). m.p. 138°–140° C., in the form of a white solid.

2-(2,3-Epoxypropoxy)-4,6-dimethylbenzophenone, used as a starting material in the above preparation, was prepared as follows:

A solution of 2-hydroxy-4,6-dimethylbenzophenone (50 g.; prepared as described by R. Baltzly et al., J. Amer. Chem. Soc., 77, 1955, 2522) in anhydrous methanol (450 ml.) was added to a methanolic solution of sodium methoxide (prepared from 5.2 g. of sodium and 200 ml. of anhydrous methanol) and the mixture was heated at reflux for 10 minutes. The solvent was evaporated and the residue was treated with anhydrous diethyl ether. The yellow solid was filtered off, dissolved in anhydrous dimethylformamide (600 ml.) and heated on the steam-bath with epichlorohydrin (88 ml.) for 2 hours. The mixture was evaporated in vacuo and the residue was treated with water. The insoluble oil was extracted with diethyl ether. The extract was dried over anhydrous sodium sulphate and evaporated in vacuo. The residue was triturated with light petroleum (b.p. 60°–80° C.) to give 2-(2,3-epoxypropoxy)-4,6-dimethylbenzophenone (40.3 g.) in the form of an off-white solid, m.p. 72°–74° C., which was pure enough for the next stage of the synthesis. A pure sample of 2-(2,3-epoxypropoxy)-4,6-dimethylbenzophenone, m.p. 74°–75° C., was obtained as a white solid by recrystallisation from cyclohexane.

EXAMPLE 2

Compounds B and D

A mixture of 2-(2,3-epoxypropoxy)-4,4',6-trimethylbenzophenone (10.0 g.), isopropylamine (10 ml.) and anhydrous methanol (50 ml.) was heated at reflux for 17 hours. The solution was then evaporated in vacuo, and the residue was dissolved in water (100 ml.) containing concentrated hydrochloric acid (10 ml.). The solution was adjusted to a pH between 6 and 7 and was shaken with ethyl acetate. The aqueous phase was then adjusted to pH 12 by the addition of aqueous sodium hydroxide solution. The precipitated oil was extracted with ethyl acetate and the extract was washed with water, dried over anhydrous sodium sulphate and evaporated. The residue was dissolved in a hot mixture of light petroleum (b.p. 40°–60° C.; 75 ml.) and cyclohexane (3 ml.) and allowed to cool slowly. The solid was filtered off and recrystallized from cyclohexane (25 ml.) to give DL-1-(3,5-dimethyl-2-p-toluoylphenoxy)-2-hydroxy-3-isopropylaminopropane (5.9 g.), m.p. 89°–91° C.

By following a similar procedure but replacing the 2-(2,3-epoxypropoxy)-4,4',6-trimethylbenzophenone used as starting material by 2-(2,3-epoxypropoxy)-2',4,6-trimethylbenzophenone, there was prepared DL-1-(3,5-dimethyl-2-o-toluoylphenoxy)-2-hydroxy-3-isopropylaminopropane, m.p. 103.5°–106° C.

The 2-(2,3-epoxypropoxy)-4,4',6-trimethylbenzophenone, m.p. 58°–60° C., and 2-(2,3-epoxypropoxy)-2',4,6-trimethylbenzophenone, m.p. 85.5°–87.5° C., used as starting materials in the above preparations, were prepared by proceeding in a similar manner to that described in Example 1 for the preparation of 2-(2,3-epoxypropoxy)-4,6-dimethylbenzophenone, but replacing the 2-hydroxy-4,6-dimethylbenzophenone by the appropriate quantities of 2-hydroxy-4,4',6-trimethylbenzophenone and 2-hydroxy-2',6,6-trimethylbenzophenone respectively.

The 2-hydroxy-4,4',6-trimethylbenzophenone, used as a starting material in the above preparation, was prepared as follows:

Anhydrous aluminium chloride (123 g.) was added in portions during 10 minutes, with stirring, to nitrobenzene 1400 ml.), allowing the temperature to rise to 40° C. 3,5-Dimethylphenyl p-toluate (109 g.) was added during 10 minutes and the mixture was heated at 60°–65° C. for 6 hours, then cooled and poured into a mixture of ice (500 g.), water (1000 ml.) and concentrated hydrochloric acid (100 ml.). The nitrobenzene was removed by steam distillation, and the cooled residue was extracted with diethyl ether (600 ml. and 2×250 ml.). The combined extracts were washed with water (3×50 ml.), dried over anhydrous sodium sulphate and evaporated in vacuo. The residue, which crystallised on cooling, was treated with light petroleum (b.p. 40°-60° C.), filtered, recrystallised from a mixture of light petroleum (b.p. 40°-60° C.) and diethyl ether and dried in a vacuum desiccator, to give 2-hydroxy-4,4',6-trimethylbenzophenone (67 g.) in the form of a pale brown solid, m.p. 102°-105° C. A pure sample of 2-hydroxy-4,4',6-trimethylbenzophenone, m.p. 103°-105.5° C., which was almost colourless, was obtained after two recrystallizations from diethyl ether.

The 3,5-dimethylphenyl p-toluate, used as a starting material in the above preparation, was prepared as follows:

p-Toluoyl chloride (154 g.) was added during 30 minutes to a solution of 3,5-dimethylphenol (122 g.) in anhydrous pyridine (200 ml.), with stirring. The temperature rose to 80° C. The mixture was stirred and heated on the steambath for 3 hours, and was then cooled and stirred with diethyl ether (500 ml.) and water (2000 ml.). The organic layer was separated, and the aqueous layer was further extracted with diethyl ether (3×250 ml.). The combined ether solutions were washed with N aqueous sodium hydroxide solution to remove unchanged starting materials and with 2 N hydrochloric acid to remove pyridine, and finally with water. The solution was dried over anhydrous sodium sulphate and evaporated in vacuo, and the residue was recrystallised from light petroleum (b.p. 40°-60° C.; 550 ml.) to give 3.5-dimethylphenyl p-toluate (203 g.). m.p. 55°-57° C.

The 2-hydroxy-2',4,6-trimethylbenzophenone, used as a starting material in the above preparation, was prepared as follows:

Anhydrous aluminum chloride (20 g.) was added in portions during 5 minutes to 3,5-dimethylphenyl o-toluate (36.3 g.) and the mixture was heated at 140°-150° C. for 3 hours. After cooling, water (300 ml.) and concentrated hydrochloric acid (25 ml.) were added and the mixture was stirred and heated on the steam-bath until hydrolysis was complete. After cooling, the mixture was stirred with diethyl ether (110 ml.) and filtered through charcoal and kieselguhr. The layers were separated and the aqueous phase was extracted with more diethyl ether (2×50 ml.). The combined ethereal solutions were washed with water, dried over sodium sulphate and evaporated in vacuo. The residue crystallised slowly. Light petroleum (b.p. 40°-60° C.; 50 ml.) was added and the solid was filtered off, washed with light petroleum (b.p. 40°-60° C.) at 0° C. and dried in a vacuum desiccator. The solid was recrystallised from methanol to give 2-hydroxy-2',4,6-trimethylbenzophenone (15.9 g.), m.p. 65°-67° C.

The 3,5-dimethylphenyl o-toluate, b.p. 192°-192.5° C./10 mm.Hg, used as a starting material in the above preparation, was prepared from 3,5-dimethylphenol by proceeding in the manner described above for the preparation of 3,5-dimethylphenyl p-toluate but replacing the p-toluoyl chloride, used as a starting material, by o-toluoyl chloride.

EXAMPLE 3

Compound C

A mixture of 2-(2,3-epoxypropoxy)-3,4,6-trimethylbenzophenone (10.0 g.), isopropylamine (10 ml.) and anhydrous methanol (100 ml.) was heated at reflux for 17 hours. The solution was evaporated in vacuo and the residue was dissolved in water (100 ml.) containing concentrated hydrochloric acid (6 ml.). The solution was filtered through charcoal and kieselguhr, adjusted to pH 11 by means of 2 N aqueous sodium hydroxide solution and extracted with ethyl acetate. The extract was washed 3 times with water, dried over anhydrous sodium sulphate and evaporated. The residue was recystallised from cyclohexane to give DL-1-(2-benzoyl-3,5,6-trimethylphenoxy)-2-hydroxy-3-isopropylaminopropane (6.6 g.), m.p. 121°-123° C.

The 2-(2,3-epoxypropoxy)-3,4,6-trimethylbenzophenone, m.p. 67°-69° C., used as a starting material in the above preparation, was prepared by proceeding in a similar manner to that described in Example 1 for the preparation of 2-(2,3-epoxypropoxy)-4,6-dimethylbenzophenone but replacing the 2 -hydroxy-4,6-dimethylbenzophenone by the appropriate quantity of 2-hydroxy-3,4,6-trimethylbenzophenone.

The 2-hydroxy-3,4,6-trimethylbenzophenone, m.p. 98°-100.5° C., used as a starting material in the above preparation of 2-(2,3-epoxypropoxy)-3,4,6-trimethylbenzophenone, was prepared by proceeding in a similar manner to that described in Example 2 for the preparation of 2-hydroxy-2',4,6-trimethylbenzophenone, but replacing the 3,5-dimethylphenyl o-toluate by the appropriate quantity of 2,3,5-trimethylphenyl benzoate (prepared as described by O. Kruber and A. Schmitt, Ber., 64, 1931, 2270).

The 2-hydroxy-3,4,6-trimethylbenzophenone has also been prepared according to the method of H. Wexler and B. Arventiev, An. Stiint., Univ. Al. I. Cuza Iasi, Sect 1c, 17, 1971, 67-71.

EXAMPLE 4

Compounds G and H

A mixture of crude 2-(2,3-epoxypropoxy)-3,6-dimethylbenzophenone (10 g.), isopropylamine (10 ml.) and dry methanol (50 ml.) was heated at reflux overnight. The solid which separated on cooling was dissolved in water (100 ml.) containing concentrated hydrochloric acid (5 ml.). The solution was adjusted to pH 8 with 2 N aqueus sodium hydroxide solution and extracted with dichloromethane (3×25 ml.). The combined extracts were dried over anhydrous sodium sulphate and evaporated. The residue was boiled with ethyl acetate (50 ml.) and then cooled to give DL-1-(2-benzoyl-3,6-dimethylphenoxy)-2-hyroxy-3-isopropylaminopropane hydrochloride (6.4 g.), m.p. 188°-191.5° C.

By proceeding in a similar manner but replacing the crude 2-(2,3-epoxypropoxy)-3,6-dimethylbenzophenone, used as starting material, by crude 4'-chloro-2-(2,3-epoxypropoxy)-4,6-dimethylbenzophenone, there was prepared DL-1-(2-p-chlorobenzoyl-3,5-dimethylphenoxy)-2-hydroxy-3-isopropylaminopropane hydrochloride, m.p. 176.5°-178.5° C.

The above crude 2-(2,3-epoxypropoxy)-3,6-dimethylbenzophenone and crude 4'-chloro-2-(2,3-epoxypropoxy)4,6-dimethylbenzophenone, used as starting materials in the above preparations of DL-1-(2-benzoyl-3,6-dimethylphenoxy)-2-hydroxy-3-isopropylaminopropane hydrochloride and DL-1-(2-p-chlorobenzoyl-3,5-dimethylphenoxy)-2-hydroxy-3-isopropylaminopropane hydrochloride respectively, were prepared in a manner similar to that described in Example 1 for the preparation of 2-(2,3-epoxypropoxy)-4,6-dimethylbenzophenone, but replacing the 2-hydroxy-4,6-dimethylbenzophenone by the appropriate quantities of 2-hydroxy- 3,6-dimethylbenzophenone (prepared as described below) and 4'-chloro-2-hydroxy-4,6-dimethylbenzophenone (prepared as described in United Kingdom Pat. Specification No. 1302299).

The 2-hydroxy-3,6-dimethylbenzophenone, used as a starting material in the above preparation of 2-(2,3-epoxypropoxy)-3,6-dimethylbenzophenone, was prepared in a manner similar to that described in Example 2 for the preparation of 2-hydroxy-2',4,6-trimethylbenzophenone, but replacing the 3,5-dimethylphenyl o-toluate by the appropriate quantity of 2,5-dimethylphenyl benzoate (prepared as described by C. G. Reid and P. Kovacic, J. Org. Chem. 34, 1969, 3308). The crude product also contained 4-hydroxy-3,6-dimethylbenzophenone. The two compounds were separated as follows;

The crude mixture was stirred with light petroleum (b.p. 40°-60° C.) and filtered. The insoluble material was 4-hydroxy-3,6-dimethylbenzophenone, m.p. 165°-168° C. The filtrate was evaporated and the residue was recyrstallized from a small volume of light petroleum (b.p. 40°-60° C.) and then from a small volume of methanol to give 2-hydroxy-3,6-dimethylbenzophenone, m.p. 111°-114° I C. This compound has also been prepared by another method by B. Arventiev, M. Strul and H. Wexler, Acad. rep. populare Romine, Filiala Iasi Studii cercetari Stiint. Chim. 11, 1960, 53.

EXAMPLE 5

Compounds E and F

A mixture of 2-(2,3-epoxypropoxy)-2', 4,5,5'-tetramethylbenzophenone (60 g.), isopropylamine (60 ml.) and dry methanol (300 ml.) was heated at reflux overnight. The solution was then evaporated in vacuo, and the residue was recrystallised from cyclohexane to give DL-1-[2-(2,6-dimethylbenzoyl)-3,5-dimethylphenoxy]-2-hydroxy-3-isopropylaminopropane (60 g.), m.p. 102°-104° C.

By following a similar procedure but replacing the 2-(2,3-epoxypropoxy)-2',4,6,6'-tetramethylbenzophenone by 2-(2,3-epoxyropoxy)-2',4,4',6-tetramethylbenzophenone, there was prepared DL-1-[2-(2,4-dimethylbenzoyl)-3,5-dimethylphenoxy]-2-hydroxy-3-isopropylaminopropane, m.p. 89°-91° C.

The 2-(2,3-epoxypropoxy)-2',4,6,6'-tetramethylbenzophenone, m.p. 108°-110° C., and 2-(2,3-epoxypropoxy)-2',4,4',6-tetramethylbenzophenone, m.p. 66°-68° C., used as starting materials in the above preparations of DL-1-[2-(2,6-dimethylbenzoyl)-3,5-dimethylphenoxy]-2-hydroxy-3-isopropylaminopropane and DL-1-[2-(2,4-dimethylbenzoyl)-3,5-dimethylphenoxy]-2-hydroxy-3-isopropylaminopropane respectively, were prepared in a manner similar to that described in Example 1 for the preparation of 2-(2,3-epoxypropoxy)-4,6-dimethylbenzophenone, but replacing the 2-hydroxy-4,6-dimethylbenzophenone by the appropriate quantities of 2-hydroxy-2',4,6,6'-tetramethylbenzophenone and 2-hydroxy-2',4,4',6-tetramethylbenzophenone respectively.

The 2-hydroxy-2',4,6,6'-tetramethylbenzophenone, m.p. 98°-100° C., and 2-hydroxy-2',4,4',6-tetramethylbenzophenone, m.p. 87°-87° C., used as starting materials in the above preparations of 2-(2,3-epoxypropoxy)-2',4,6,6'-tetramethylbenzophenone and 2-(2,3-epoxypropoxy)-2', 4,4',6-tetramethylbenzophenone respectively, were prepared in a manner similar to that described in Example 2 for the preparation of 2-hydroxy-4,4',6-trimethylbenzophenone, but replacing the 3,5-dimethylphenyl-p-toluate by the appropriate quantities of 3,5-dimethylphenyl 2,6-dimethylbenzoate and 3,5-dimethylphenyl 2,4-dimethylbenzoate respectively.

The 3,5-dimethylphenyl-2,6-dimethylbenzoate, m.p. 95°-97° C., and 3,5-dimethylphenyl 2,4-dimethylbenzoate, m.p. 34°-36° C., used as starting materials in the above preparations of 2-hydroxy-2',4,6,6'-tetramethylbenzophenone and 2-hydroxy-2',4,4',6-tetramethylbenzophenone respectively, were prepared in a manner similar to that described in Example 2 for the preparation of 3,5-dimethylphenyl p-toluate, but replacing the p-toluoyl chloride by the appropriate quantities of 2,6-dimethylbenzoyl chloride and 2,4-dimethylbenzoyl chloride.

EXAMPLE 6

Compound I

A mixture of 2-(2,3-epoxypropoxy)-4,4',6-trimethylbenzophenone (10 g.), t-butylamine (10 ml.) and dry methanol (50 ml.) was heated at reflux overnight. The mixture was evaporated in vacuo, and the residue was recrystallized from cyclohexane to give DL-1-t-butylamino-3-(3,5-dimethyl-2-p-toluoylphenoxy)-2-hydroxypropane (7 g.), m.p. 116°-118° C.

The 2-(2,3-epoxypropoxy)-4,4', 6-trimethylbenzophenone, used as a starting material in the above preparation, was prepared as described in Example 2.

EXAMPLE 7

Compound J

A mixture of 2-(2,3-epoxypropoxy)-4,4', 6-trimethylbenzophenone (10 g.), 2-phenylethylamine (10 ml.) and dry methanol (50 ml.) was heated at reflux overnight and was then evaporated in vacuo. The residue was dissolved in ethyl acetate (400 ml.) and the solution washed with water (3×50 ml.) and dried over anhydrous sodium sulphate and evaporated. The residue was dissolved in ethanol and an excess of a solution of hydrogen chloride in diethyl ether was added. The solid which separated was filtered off and recrystallized from ethanol to give DL-1-(3,5-dimethyl-2-p-toluoylphenoxy)-2-hydroxy-3-(2-phenylethylamino)-propane hydrochloride (8 g.), m.p. 209°-211° C.

The 2-(2,3-epoxypropoxy)-4,4', 6-trimethylbenzophenone, used as a starting material in the above preparation, was prepared as described in Example 2.

EXAMPLE 8

A solution of DL-1-(3,5-dimethyl-2p-toluoylphenoxy)-2-hydroxy-3-isopropylaminopropane (0.5 g.; prepared as described in Example 2) in dry diethyl ether was treated with excess solution of hydrogen chloride in diethyl ether.

The resulting gum was scratched with diethyl ether to form DL-1-(3,5-dimethyl-2-p-toluoylphenoxy)-2-hydroxy-3-isopropylaminopropane hydrochloride (0.4 g.), in the form of a white solid, m.p. 121°-123° C.

The present invention includes within its scope pharmaceutical compositions which comprise at least one of the benzophenone derivatives of general formula I, or a non-toxic acid addition salt thereof, in association with a pharmaceutically-acceptable carrier or coating. In clinical practice the compounds of the present invention will normally be administered orally or parenterally.

Solid compositions for oral administration include compressed tablets, pills, powders and granules. In such solid compositions, one or more of the active compounds is, or are, admixed with at least one inert diluent such as starch, sucrose or lactose. The compositions may also comprise as is normal practice, additional substances other than inert diluents, e.g. lubricating agents such as magnesium stearate.

Liquid compositions for oral administration include pharmaceutically-acceptable emulsions, solutions, suspensions, syrups and elixirs containing inert dileunts commonly used in the art such as water and liquid paraffin. Besides inert diluents such compositions may also comprise adjuvants, such as wetting and suspending agents, and sweetening, flavouring, perfuming and preserving agents. The compositions according to the invention for oral administration also include capsules of absorbable material, such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage shall be obtained. Obviously, several unit dosage forms may be administered at about the same time. The dose employed depends upon the desired therapeutic effect, the route of administration and the duration of the treatment. In the adult, the doses are generally between 0.1 and 10, more particularly between 0.1 and 1, mg./kg. body weight per day by oral administration, for example in the treatment of migraine.

The following Examples illustrate pharmaceutical compositions according to the invention.

EXAMPLE 9

Tablets of the formula:

| | |
|---|---|
| DL-1-(3,5-dimethyl-2-p-toluoylphenoxy)-2-hydroxy-3-isopropylaminopropane hydrochloride | 20 mg. |
| lactose | 49.5 mg. |
| starch | 20 mg. |
| dextrin | 20 mg. |
| magnesium stearate | 0.5 mg. | were prepared by intimately mixing the amine hydrochloride, lactose, starch and dextrin and passing the mixture through a 60-mesh British Standard sieve. After addition of the magnesium stearate, the mixture was granulated to a suitable size and the granules were compressed to form tablets.

EXAMPLE 10

An injectable solution of the following composition:

| | |
|---|---|
| DL-1-(3,5-dimethyl-2-p-toluoylphenoxy)-2-hydroxy-3-isopropylaminopropane hydrochloride | 2.5 g. |
| distilled water | to 100 ml. | was prepared by dissolving the amine hydrochloride in the distilled water. The solution was filtered and filled into ampoules which were sterilised in an autoclave.

EXAMPLE 11

Tablets of the formula:

| | |
|---|---|
| DL-1-(2-benzoyl-3,5-dimethylphenoxy)-2-hydroxy-3-isopropylaminopropane hydrochloride | 20 mg. |
| lactose | 49.5 mg. |
| starch | 20 mg. |
| dextrin | 20 mg. |
| magnesium stearate | 0.5 mg. | were prepared by intimately mixing the amine hydrochloride, lactose, starch and dextrin and passing the mixture through a 60-mesh British Standard sieve. After addition of the magnesium stearate, the mixture was granulated to a suitable size and the granules were compressed to form tablets.

EXAMPLE 12

An injectable solution of the following composition:

| | |
|---|---|
| DL-1-(2-benzoyl-3,5-dimethylphenoxy)-2-hydroxy-3-isopropylaminopropane hydrochloride | 2.5 g. |
| distilled water | to 100 ml. | was prepared by dissolving the amine hydrochloride in the distilled water. The solution was filtered and filled into ampoules which were sterilised in an autoclave.

We claim:

1. A benzophenone derivative of the formula:

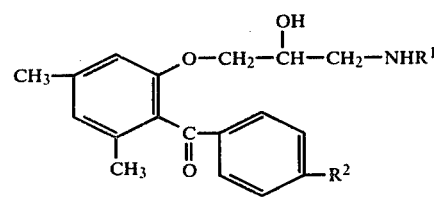

wherein $R^1$ is isopropyl, t-butyl, or 2-phenylethyl, and $R^2$ is hydrogen, methyl, or chlorine, and non-toxic acid addition salts thereof.

2. A benzophenone derivative according to claim 1 which is DL-1-(2-benzoyl-3,5-dimethylphenoxy)-2-hydroxy-3-isopropylaminopropane, and non-toxic acid addition salts thereof.

3. A benzophenone derivative according to claim 1 which is DL-1-(3,5-dimethyl-2-p-toluoylphenoxy)-2-hydroxy-3-isopropylaminopropane, and non-toxic acid addition salts thereof.

4. A benzophenone derivative according to claim 1 which is DL-1-(2-p-chlorobenzoyl-3,5-dimethylphenoxy)-2-hydroxy-3-isopropylaminopropane, and non-toxic acid addition salts thereof.

5. A benzophenone derivative according to claim 1 which is DL-1-t-butylamino-3-(3,5-dimethyl-2-p-toluoylphenoxy)-2-hydroxypropane, and non-toxic acid addition salts thereof.

6. A benzophenone derivative according to claim 1 which is DL-1-(3,5-dimethyl-2-p-toluoylphenoxy)-2-hydroxy-3-(2-phenylethylamino)propane, and non-toxic acid addition salts thereof.

7. A pharmaceutical composition which comprises, as active ingredient, a benzophenone derivative as claimed in claim 1, or a non-toxic acid addition salt thereof, in association with a significant amount of a pharmaceutically-acceptable carrier.

8. A method for the treatment of migraine which comprises administering orally to a person with migraine between 0.1 and 10 mg./kg. body weight of a benzophenone derivative as claimed in claim 1 or a non-toxic salt thereof.

9. A method according to claim 8 in which the benzophenone derivative is DL-1-(2-benzoyl-3,5-dimethylphenoxy)-2-hydroxy-3-isopropylaminopropane or a non-toxic salt thereof.

10. A method according to claim 8 in which the benzophenone derivative is DL-1-(3,5-dimethyl-2-p-toluoylphenoxy)-2-hydroxy-3-isopropylaminopropane or a non-toxic acid addition salt thereof.

* * * * *